United States Patent [19]
Gill et al.

[11] Patent Number: 5,139,511

[45] Date of Patent: Aug. 18, 1992

[54] EXPANSIBLE CANNULA

[76] Inventors: Steven S. Gill, 184 Woodlands Road, Woodlands, Nr. Southampton, S04 2GL, England; Joseph F. Jackson, The Hawthornes, Central Park, Halifax, West Yorkshire, England

[21] Appl. No.: 654,813

[22] Filed: Feb. 13, 1991

[30] Foreign Application Priority Data

Feb. 14, 1990 [GB] United Kingdom ................ 9003379

[51] Int. Cl.⁵ ............................................ A61M 29/00
[52] U.S. Cl. ........................................ 606/198; 128/3
[58] Field of Search ............................... 606/191–198; 604/104–107, 153, 264, 272, 280, 281, 185; 128/3

[56] References Cited

U.S. PATENT DOCUMENTS 4,899,729  2/1990  Gill et al. ............................ 606/198

Primary Examiner—C. Fred Rosenbaum
Assistant Examiner—M. Mendez
Attorney, Agent, or Firm—Richard E. Jenkins

[57] ABSTRACT

The invention provides an expansible cannula (particularly useful as a trocar) comprising essentially a conical tube made of metal foil with its proximal end located in a holder, and an expander tube which can be pushed through the stem from the proximal end, to cause the stem to expand from its conical free condition to a distended cylindrical condition. The stem itself comprises a caudex which has only radial motion on expansion of the stem, and a leaf, which in addition to uncoiling on expansion of the stem is also permitted a degree of forward motion, so that the front end of the stem becomes circular in the opened condition.

10 Claims, 3 Drawing Sheets

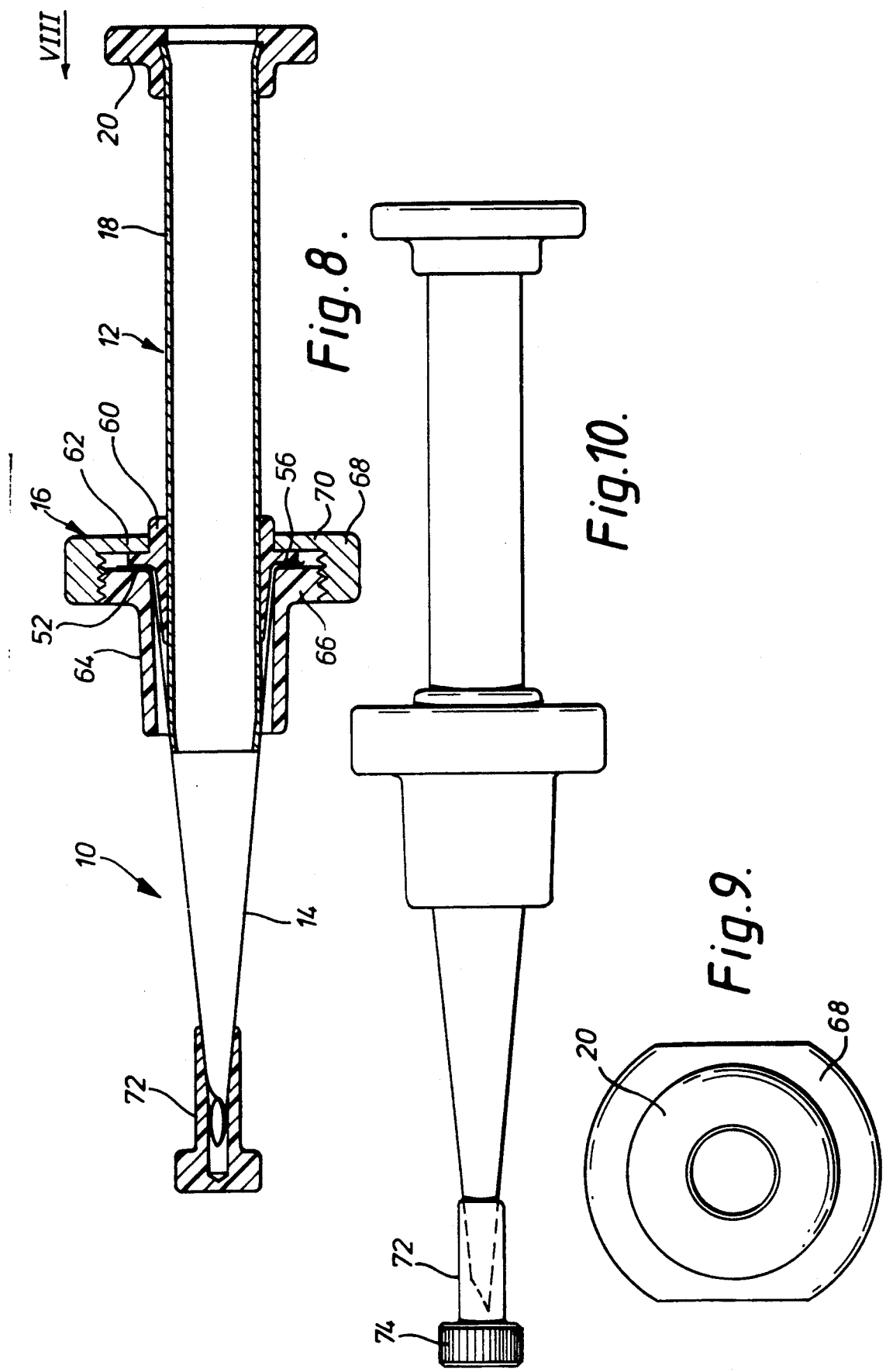

EXPANSIBLE CANNULA

The invention is concerned with a surgical appliance intended to be used to facilitate the introduction of instruments, scopes, tubing or other investigative and surgical equipment through the skin and tissue of a patient into body cavities or organs. More particularly, the invention provides a device (referred to as a cannula) which can be inserted through a relatively small incision in the skin and tissue and then expanded, dilating the tissue, to provide a guide channel through the skin and other body tissues, to form a tube through which the surgical equipment can pass to the target lesion for the performance of investigative or therapeutic procedures.

The cannula are useful in the treatment of humans and will be so described herein, but it should be understood that they could also be applied in veterinary practice. It is also to be understood that the expression "cannula" is used herein as a generic term for any appliance which is capable of providing a passage through body tissue. The specific embodiment described hereinafter is in fact intended to be used primarily for insertion through the rib cage of a patient and might therefore be more precisely defined as a trocar, but the broader expression "cannula" is used, because the invention is applicable to items which would not strictly be described as trocars.

In the Specification of European Patent Application EU-A-206553 (GILL and JACKSON) there is described an expansible cannula comprising a conical tubular stem which is formed of thin sheet material, such as beryllium copper, the sheet material being coiled or partially coiled, so that it is capable of opening up from a closed condition by reducing the cone angle thereby increasing the diameter of the stem at the distal end. Opening up of the stem is achieved by inserting an expander tube through the stem from the proximal end, so that as the tube moves forwardly (i.e. towards the distal end) it engages with the inner surface of the conical tube, and opens up the tube into a more cylindrical shape.

The cannula described in European Specification EU-A-206533 is particularly useful where a relatively deep penetration is required, so that the cannula itself is long relatively to its diameter. (Typically, the expanded internal diameter of the cannula need be no more than about 10 millimeters and this requires an initial incision of only about 10 millimeters length, to allow the cannula to be introduced in its closed condition). However, for some purposes, a relatively short cannula is desirable, especially where it is required to transmit relatively large lateral forces, as when the cannula is forced between adjacent ribs and the ribs have to be prised apart. Since the required internal diameter of the expanded cannula remains about the same (e.g. 10 millimeters) a shorter cannula has to have a wider cone angle in the closed condition and the opening action becomes more severe. The proximal end of the stem is completely restrained against axial motion, but in expanding the stem from the conical "free" condition towards the cylindrical condition, some of the stem is under a force tending to move it fowardly (i.e. towards the distal end). At best, this tends to distort the stem, and in some instances, it may actually tear the stem. The cannula becomes unstable it is actually torn.

Furthermore, the opening of a coiled conical stem as described in EU-A-206553 tends to produce a helical leading edge which does not completely circumscribe the leading end of the expanded tube.

It is the object of the invention to provide an expansible cannula which is an improvement on the cannula described in Eu-A-206553 particularly in relation to a relatively short cannula.

According to this invention an expansible cannula comprises a stem and a holder, the stem taking the form of a conical coiled foil retained at its larger diameter proximal end in the holder in a circular shape; biased by its own resilience into the concial coiled "free" condition and adapted to uncoil from the conical shape into a substantially cylindrical shape when a cylindrical expander is forced into and along it from the proximal end, and is characterised in that the foil stem comprises a tapering caudex anchored to the holder at its proximal end in a manner which will permit rocking on its anchorage in outward radial motion only, as required to permit the caudex to move from its closed location where it forms part of the conical shape of the stem, to the fully open location where it forms parts of the cylindrical shape of the stem, and a leaf portion attached to one longitudinal edge of the caudex along substantially the entire length of its parallel edges, and arranged, so that when in the coiled "free" condition its distal edge forms a helix subtending at least 360° around the longitudinal axis of the stem, the helix angle being such that the proximal extremity of the distal edge is spaced a substantial part of the total length of the stem from its distal extremity; the proximal end of the leaf portion being constrained by the holder in a manner which gives it freedom for both circumferential motion (uncoiling) and longitudinal motion, so that the helix angle of the distal edge of the leaf portion reduces to zero or near zero when the stem is expanded into the open condition, to provide the necessary leaf material at the distal extremity of the stem to form the substantially cylindrical from in the open condition, but the holder preventing movement of the proximal end of the leaf portion outside the cylindrical form dictated by the holder.

Since the leaf portion is coiled into a cone, the distal edge must of necessity take up a helical formation, and the greater the cone angle, the greater the pitch of the helix—which is why the helical edge at the distal end is of more significance in a relatively short cannula than it is in a relatively long one. Because the distal edge subtends more than 360°, the end part of the distal edge up to its overlap position, forms a complete circle about the axis of the stem.

The expander is only protected from engagement with tissues at the distal end of the cannula up to the position of overlap, beyond that position the expander would only be partially protected were it to project through the oblique edge at the distal end of the stem. Because the invention provides for some longitudinal motion of the leaf during uncoiling (expansion) the distal edge of the leaf changes from a helical to a substantially circular form (i.e. the helix angle reduces to zero) and the distal end of the stem forms a complete tube thus adapting it to sustain lateral forces and protecting the distal end of the expander tube.

Preferably the complete distal edge of the leaf in the closed condition extends through a helix the length of which is not less than 10% of the total length of that part of the stem which projects from the holder. It is further preferred that the stem is provided with a sharp point at its distal extremity and in that a cylindrical expander for the cannula is adapted so that when fully inserted, it projects beyond the point.

According to another preferred feature of the invention, the end edges of the stem taper towards each other from the longitudinal edge which is attached to the caudex, the proximal end being bowed outwardly. It is also preferred that the caudex has a generally triangular shape and is wide enough at the proximal end to subtend approximately 180° around the stem, there being two laterally spaced tabs on the proximal end of the caudex which are nipped ion the circular holder, wherein the lateral spacing of the tabs on the caudex forms a circumferential spacing when the stem is retained in the holder.

According to another preferred feature of the invention, the caudex and stem is made in sheet metal which is heat treated after coiling to give it the required resilience. Preferably the stem is made in beryllium copper.

According to yet another preferred feature of the invention, the proximal end of the stem is clamped by fitting two tubular elements one inside and one outside the proximal end of the coiled stem and securing the two tubular elements together. Preferably the tubular element which fits into the end of the stem has a collar, and the tubular element which fits over the stem has a flange, the tabs on the caudex of the stem being nipped between the collar and the flange, there being a nut engaging with the outer end of the collar and having screw-threaded engagement with the tubular element which fits over the stem.

It is also preferred that an end cap is provided which is a push fit on the distal end of the stem in the closed condition, for protecting the sharp point at the distal extremity of the stem.

Further preferred features of the invention, will become apparent, from the following description of an expansible cannula, in accordance with the invention, which is described here by way of example only, with reference to the accompanying drawings, in which.

Figure 3:
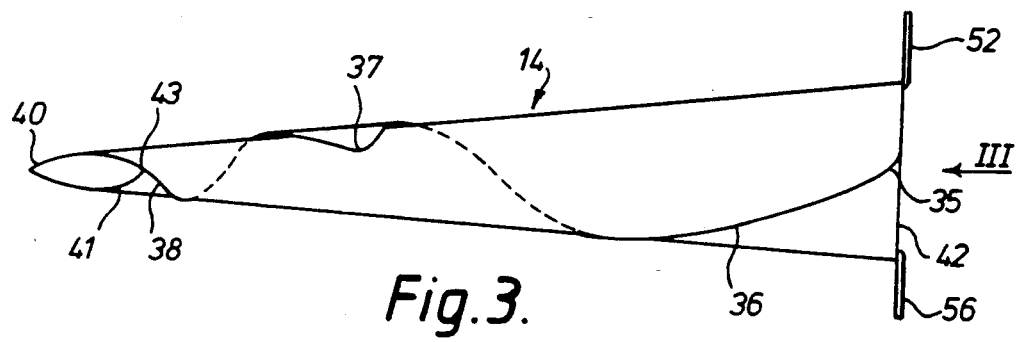
FIG. 3 is a side elevation of a stem formed by coiling the blank shown in FIG. 2.
Figure 4:
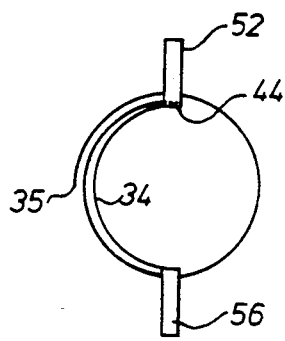
FIG. 4 is an end view looking in the direction of the arrow III in FIG. 3.
Figure 5:
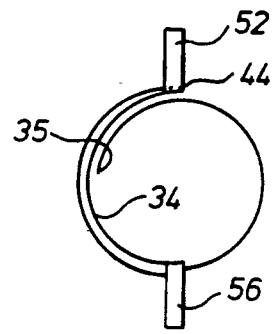
Figure 6:
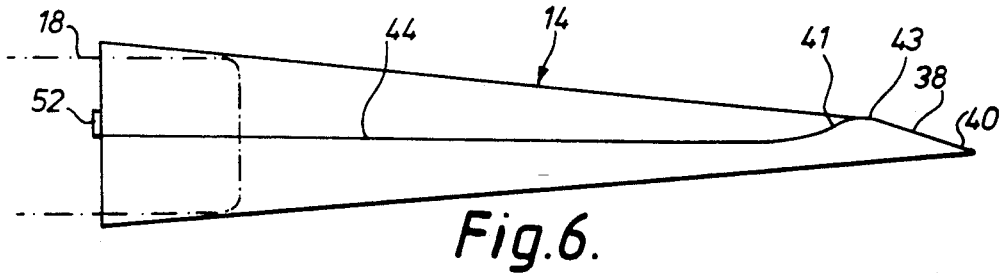
Figure 7:
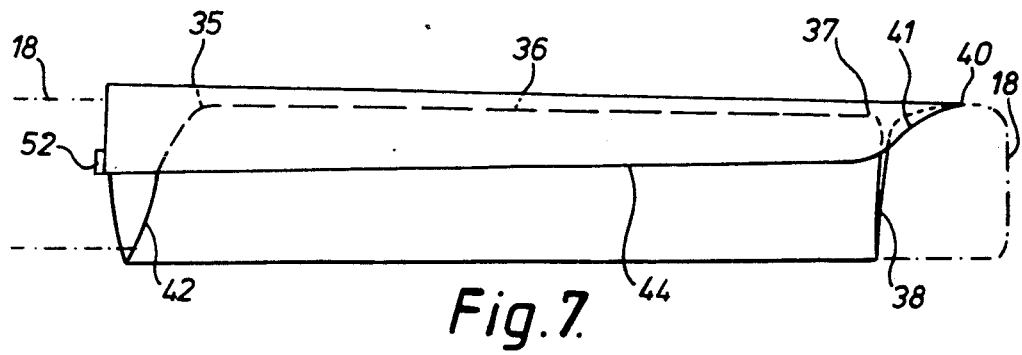

FIG. 5 is an end view similar to FIG. 4, but showing the stem being turned inside-out as part of the manufacturing process, FIG. 6 is an elevation similar to FIG. 3 (but with the stem pointing in the opposite direction) to show the external appearance after the turning inside-out operation, FIG. 7 is an elevation similar to FIG. 6, but showing the stem in the opened condition, FIG. 8 is a longitudinal cross-section through an assembled cannula incorporating the stem shown in FIG. 6, FIG. 9 is an end view looking in the direction of the arrow VIII in FIG. 8 and FIG. 10 is a plan view of the cannula shown in FIG. 8.

The principal elements of the cannular which forms the illustrated specific embodiment, are the cannula 10, and a tubular expander 12, which as illustrated in FIGS. 8 and 10 is inserted into the proximal end of the cannula 10. Before describing the construction of the cannula in detail, it will be mentioned, that the cannula comprises a stem 14 which in the "free" or unrestrained condition takes the form of a conical tube tapering downwardly from its proximal end, the proximal end of the stem being located within a holder 16, which besides retaining the proximal end of the stem in a manner to be hereinafter described, also provides a convenient means whereby the person using the cannula is able to grip the distal end of the cannula in order to carry out an operation.

The tubular expander 12, comprises a length of stainless steel tube which in this specific embodiment is of approximately 10 millimeters internal diameter, extending from a disc-like plastics gripping piece 20, by means of which the operator is able to grip the proximal end of the expander tube for inserting it into the cannula 10, and then pushing it forward relatively to the cannula. It will be noted, that the distal end of the expander tube 12 is slightly tapered inwardly, to assist in inserting it into the stem 14.

The stem 14 is manufactured from a blank 30 (see FIG. 1) of thin metal foil, and beryllium copper has been found suitable for this purpose. It will be appreciated, that the material chosen for the stem should be insert, relatively to body acids, but, as will hereinafter appear, it must also be capable of exhibiting a relatively high degree of resilience.

The blank 30 itself comprises a main portion 32, and a triangular caudex portion 34. The main portion 32 has a straight bottom longitudinal edge 36; a front edge 38 which inclines forwardly from the bottom edge 36, and terminates in a pointed portion 40; a rear edge 42 which is bowed outwardly, and a top edge 44 which is constituted by a fold line indicated in dotted lines in FIG. 1, between the main portion 32 and the triangular portion 34. An edge 41, which is bowed inwardly, joins the front extremity of edge 44 to the point 40. The triangular portion itself joins the main portion 32 at its front end a short distance to the rear of the point 40, and at its rear proximal end, comprises a pair of "teeth" 46 and 48 separated by a gap 50.

At the stage where the blank 30 is cut from the sheet of beryllium copper foil, the metal has no imparted resilience, in other words, it only has the natural resilence of the material itself.

Figure 1:
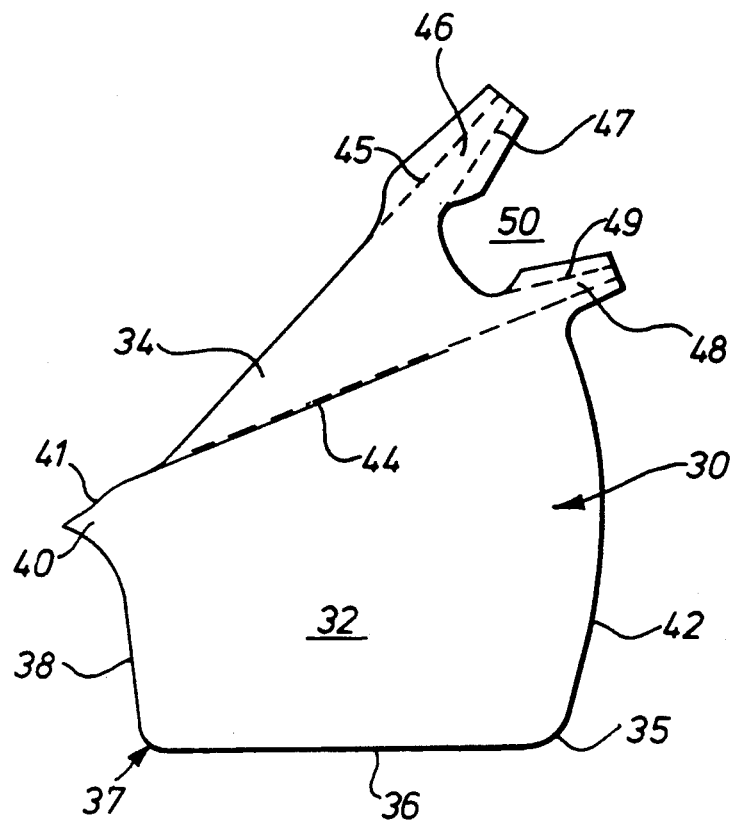
FIG. 1 is a plan view of a foil blank.
Figure 2:
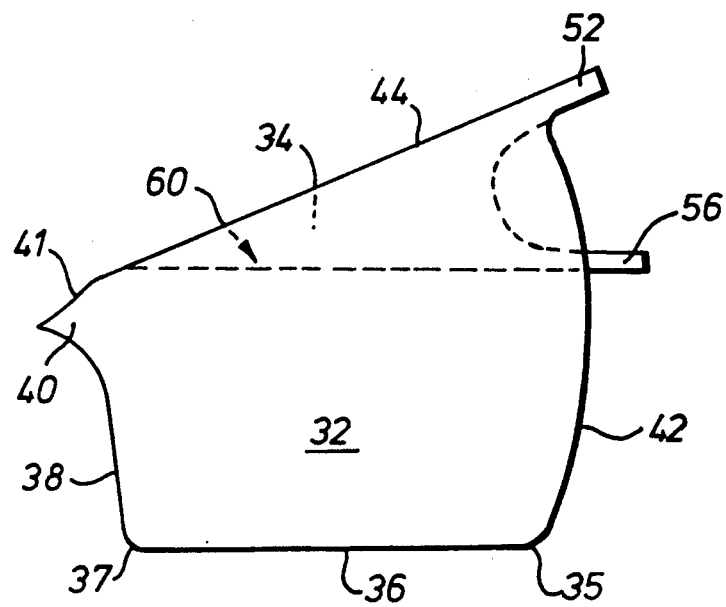
FIG. 2 is a plan view of the foil blank shown in FIG. 1, but after several folds have been made.

As a first stage in the manufacture of the stem 14, the blank 1 is folded along the four fold lines indicated in FIG. 1 at 44, 45, 47 and 49, so that it adopts the shape indicated in FIG. 2, where the triangular reinforcing portion 34 lies under part of the main portion 32 and teach "tooth" 46 and 48 is formed in to a narrower rigid tab by virtue of the folding over of the marginal portions of the outsides of the old lines 44, 45, 47 and 49. Both the tabs 52 and 56 extend from the triangular folded over portion 34. It will be appreciated that the tabs have a greater rigidity than the remainder of the blank. The folded-over triangular portion with the tabs 52 and 56, will be referred to hereinafter as the caudex 60 of the stem. The remaining part of the blank then forms a leaf, and this portion is generally trapezoidal in shape, having nearly parallel edges 38 and 42 and non-parallel edges 44 and 46. The front edge 38 is inclined and the rear edge 42 is bowed. The front edge 38 meets the bottom edge 36 at a rounded corner 37. The rear edge 42 meets the bottom edge 36 at a rounded corner 35.

The blank having the form illustrated in FIG. 2 is then coiled on itself turning the caudex 34 inwardly as illustrated in FIG. 4, to provide a conical tube, the shape of which is illustrated in FIG. 3. By virtue of the bowed shape of the edge 42 it is possible to form the proximal end of the tube into a spiral formation as illustrated in FIG. 4, wherein the gaps between the convolutions are generally exaggerated for clarity, but so as to produce a proximal edge which is at right angles to the longitudinal axis of the stem.

When the blank is coiled into the conical tube as illustrated in FIG. 3, the bottom and front edges of the blank 36 and 38 respectively adopt helical forms of opposite pitch. These edges meet at the corner 37, which is now the termination of the outer turn of the conical tube, and it will be observed that in the particular example illustrated, the point 37 is displaced about 30% of the total length of the stem from the distal extremity. Generally this distance will not be less than 10% of the total length of the stem.

At the distal end of the stem, an oblique oval shaped opening is formed by the helical edges 38 and 41. These edges meet at the distal extremity at the point 40, and a short distance proximally they together circumvent a full circle at a position 43 where the edge 38 overlaps the edge 41. In this condition, the stem 14 is submitted to a heat treatment to give it a permanent "set" and a considerable degree of inherent resilience. In other words, the stem will attempt to revert to the form shown in FIG. 3, if it is distended in any way from that form. The actual heat treatment needs no explanation, as it is conventional.

At this stage the stem is turned inside-out. This is achieved by distending the coiled stem, until the helical outer edges 36 and 38, meeting at the corner 37, can be introduced under the remaining coiled part of the stem, and the action is continued until the stem is turned completely inside-out from the condition illustrated in FIGS. 3 and 4. The result is illustrated in FIGS. 5 and 6. The helical edge 36 and the proximal and greater portion of the helical edge 38 are then on the inside, and the outer edge of the stem is formed by the fold line 44. It is to be observed, that this outer edge extends in a straight longitudinal line rather than the helical formation adopted by the edges 36 and 38. This is an important feature of the construction, because it is easier to force the stem through an incision, if the outer edge of the coiled portion of the stem is a straight longitudinal edge rather than a helical one. There is still an oblique, oval shaped opening formed by the helical edges 38 and 41.

Turning now to FIGS. 8, 9 and 10, it will be seen that the holder 16 includes an inner guide sleeve 60, which is made in plastics material, such as nylon. The bore of the sleeve 60 is a sliding fit on the exterior of the tube 18, so that it provides a guide for that tube when it is introduced into the cannula 10. Externally, the guide sleeve 60 has a collar 62. An outer sleeve member 64 is provided, which is also made in plastics material, and the bore of the outer member 64 is such that it is a clearance fit around the larger, proximal, end of the stem 14, when the latter is in the "free" condition illustrated in FIG. 6. The cannula is assembled, by threading the stem 14 through the bore of the outer member 64 to bring its tabs 52 and 56 into engagement with the proximal end of a flange 66 on the outer member 64, and then the guide sleeve 60 is inserted into the proximal end of the stem 14, to bring its collar 62 into engagement with the tabs 52 and 56. To complete the assembly, a nut 68 also made in plastics material is screwed on to a screw-thread formed on the flange 66 of the outer member 64, an internal flange 70 of the nut 68 engaging with the collar 62 on the guide sleeve 60. When this nut is tightened, the sleeve 60 and the outer sleeve 64 are drawn together, nipping the tabs 52 and 56 between them. The stem 14 of the cannula is then held securely to the holder 16 by the nipping of the tabs 52 and 56.

A plastics cap 72, having a knurled head 74 is a push fit over the distal end of the stem 14 in the "free" condition of the stem, and this cap 72 provided for the purpose of protecting the sharply pointed end 40 of the stem 14.

It is now possible to describe the operation of the apparatus.

Once an incision has been made through the skin and tissue of the patient, the cap 72 is removed, and then the operator grips the holder 16 in his hand, and pushes the sharp distal end 40 of the cannula through the incision. The concial shape of the cannula in the "free" condition facilitates controlled entry of the cannula through the incision. The depth of penetration of the stem 14 though the incision can be accurately controlled by the operator, partly because of the controlled entry combined with the short length of the stem 14, and partly because of the handgrip facility. Moreover, because the external edge 44 on the stem is straight, it does not inhibit the forcing of the stem through the tissue.

When the cannula is in place, the expander tube 12 resting on the proximal end of the cannula, is then pushed forwardly in a controlled manner. This may be achieved by the operator gripping the holder 16 with the index and middle fingers engaging under the flanges 66, and pushing forward the expander tube, with the thumb placed over the gripping piece 20 on its proximal end. As the tube penetrates further into the stem 14, it gradually opens up that stem to allow the tube to pass. The part of the cannula which has passed through the incision will usually be in engagement with body tissues. Because the stem opens up gradually and evenly from the conical to the cylindrical shape, it expands the tissues relatively easily with reduced trauma then is the case when a generally cylindrical cannula is pushed through an incision into tissues.

During the opening up action, the caudex 60 cannot move longitudinally but simply pivots on its tabs 52 and 56, so that its distal end moves through an arc, and consequently the caudex has only a radially outward motion. However, the leaf 32 of the stem has a compound opening action. To begin with, it uncoils to allow the cone angle to reduce and eventually, when the distal end of the expander tube 12 projects out at the distal end of the stem 14, the entire stem of the cannula forms a cylindrical tube as illustrated in FIG. 7. The outer member of the holder 64 (as illustrated in FIG. 8) restricts the opening of the proximal end of the stem, so that the proximal end does not expand beyond the parallel-sided cylindrical form. That ensures the other component of motion of the leaf 32, that is, it is able to move forwardly to some extent (i.e. towards the distal end), because it is not anchored in the holder at its proximal end.

The fact is that when the stem is opened from its "free" conical form to the cylindrical form, the distal edge 38 changes from a helix extending over a length which may be considerably greater than 10% of the total length of the stem itself (see FIG. 3) to a completely circular condition in a single longitudinal plane (see FIG. 7). The helix angle of the edge 38 therefore reduces to zero to form the complete 360° distal edge of the opened stem. In addition, the helical edge 36 changes to a longitudinal edge substantially parallel with the axis of the stem when the stem is opened.

This compound action f the leaf is important because it provides complete protection for the distal end of the expander tube 12 during the last part of the motion of that tube when its distal extremity is passing through the distal end of the stem 14.

When the expander tube 12 is fully in place so that the holder 20 engaged with the guide sleeve 60, the distal end of the expander tube projects beyond the sharp distal extremity of the opened stem 40, as illustrated in FIG. 7. This protects the tissues from damage that may have otherwise occurred if the tissues had come into contact with the sharp point when the device is manipulated.

With the expansible cannula so opened, it is then possible to introduce drainage tubing or instruments through the bore of the expander tube 12 to the lesion. When the therapeutic or investigative procedure has been completed the expansible cannula is withdrawn from the tissues while in its opened condition.

The embodiment of the invention herein described has particular application to the insertion of thoracic drains into the chest for the drainage of abnormal intrapleural collections of air, blood, pus etc., compromises ventilation.

Insertion of an intrapleural drain using the expansible cannula is preceded by cleaning the skin at the proposed site of entry and infiltrating the skin and intercostal space with local anaesthetic. Having infiltrated the space the needle is advanced into the pleural cavity and the syringe plunger withdrawn to aspirate its contents. This is an important step ensuring that the correct intrapleural targer has been reached and that it contains the expected contents be it air, blood or pus. A skin incision approximately 1 centimeter long is then made and the expansible cannula inserted through it. The finely tapering cannula will then pass with little resistance through the intercostal muscles and into the pleural space. On entering the pleural space, a hiss or air or back flow down the cannula will indicate to the operator that it is correctly placed. The cannula can then be expanded from its conical to cylindrical shape as described above by depressing the expander tube 18 in its proximal end with a syringe like action.

A chest drain is next passed through the cannula and directed towards the apex of the lung or other site. The expansible cannula is then withdrawn around the catheter leaving the catheter alone in situ. By using a chest catheter which is sealed at its proximal end air is prevented from entering the chest until its end is cut off and connected to an underwater seal drain. This allows the clinician to secure the catheter to the chest wall in his own time and avoids the use of clamps which have a tendency to pull an unsecured drain out of the chest.

The method of chest drain insertion using the expansible cannular herein described has considerable advantages over existing methods. Its short length ensures that there is no risk of plunging deep into interthoracic or subdiaphragmatic organs with potentially fatal consequences. The fine tapered shape of the cannula facilitates easy passage through the tissues giving the operator full control of the insertion and allowing him to feel his way into the pleural cavity. If the operator fails to carry out the usual checking procedures and inadvertently introduces the cannula into the wrong position then there will be no hiss of air or back flow of fluid down the cannula. This is an indication that the target has not been reached and so the cannula will not be opened. In these circumstances, if the tip of the cannula has penetrated the lung then this will at worst be a small puncture hole and of little consequence. When the device is in its open condition, the expander tube projects beyond the distal end of the cannula's metal foil leaf 32 (see FIG. 7). This allows the device to be manipulated freely within the pleural cavity without risk of injury to the surrounding tissues. Only the soft chest drain catheter passes deeply into the chest.

In addition to these important safety features the expansible cannula has other advantages over existing methods of chest drain insertion. When the device is opened it undergoes a true radial expansion which stretches the intercostal muscles and causes minimal trauma. The subsequent tight grip of the intercostal muscles on the chest drain prevents air from leaking around the drain, reduces the risk of infection spreading along the passage and assists in holding the drain in position. When the drain is removed, the intercostals further contract obliterating the passage, and reducing the risk of air fistual formation. This is in contrast to the conventional method of thoracic drain insertion, where a formal dissection through the chest wall (which may be 3–4 centimeters thick) requires a comparatively wide exposure and cutting of the intercostal muscles. This is a more traumatic procedure accompanied by increased risk of hemorrhage and secondary infection. The cut or torn intercostals fail to form a tight seal around the drain and so the advantages outlined above are lost.

We claim:

1. An expandable cannular comprising a stem, a holder and a cylindrical expander; wherein the stem is in the form of a conical coiled foil; the holder retaining the stem at its larger diameter proximal end in a circular shape; the stem being biased by its own resilience into the conical coiled "free" condition but capable of uncoiling from the conical shape into a substantially cylindrical shape, the expander being so dimensioned that when it is forced into and along the stem from the proximal end, it causes the stem to expand into the cylindrical shape and wherein the foil stem itself comprises: a tapering caudex anchored to the holder at its proximal end in a manner which will permit rocking on its anchorage in outward radial motion only when the expander is used to expand the stem, as required to permit the caudex to move from its closed location where it forms part of the conical shape of the stem to the fully open location where it forms part of the expanded cylindrical shape of the stem, and a leaf portion attached to one longitudinal edge of the caudex along substantially the entire length of its parallel edges, and arranged so that when in the "free" condition its distal edge forms a helix subtending at least 360° around the longitudinal axis of the stem, the helix angle being such that the proximal extremity of the distal edge is spaced a substantial part of the total length of the stem from its distal extremity; the proximal end of the leaf being constrained by the holder in a manner which gives it freedom for both circumferential motion (uncoiling) and longitudinal motion, so that the helix angle of the distal edge of the leaf portion reduces to zero or near zero when the stem is expanded into the open condition, to provide the necessary leaf material at the distal extremity of the stem to form the substantially cylindrical form in the open condition, but the holder preventing movement of the proximal end of the leaf portion outside the cylindrical form dictated by the holder.

2. An expansible cannula according to claim 1, wherein the complete 360° distal edge of the leaf in the closed condition extends through a helix the length of which is not less than 10% of the total length of that part of the stem which projects from the holder.

3. An expansible cannular according to claim 1 or claim 2, wherein the stem is provided with a sharp point at its distal extremity and the expander is of such a length that when fully inserted into the stem, it projects beyond the point.

4. An expansible cannular according to claim 1 or claim 2, in which the end edges of the stem taper towards each other from the longitudinal edge which is attached to the caudex, the proximal end being bowed outwardly.

5. An expansible cannular according to claim 1 to claim 2, wherein the caudex has a generally triangular shape and is wide enough at the proximal end to subtend approximately 180° around the stem, there being two laterally spaced tabs on the proximal end of the caudex which are nipped in the circular holder, the lateral spacing of the tabs on the caudex forming a circumferential spacing when the stem is retained in the holder.

6. An expansible cannula according to claim 1 or claim 2, wherein the caudex and stem are made in sheet metal which is heat treated after coiling to give it the required resilience.

7. An expansible cannular according to claim 6, wherein the stem is made in beryllium copper.

8. An expansible cannular according to claim 1 or claim 2, wherein the holder comprises two tubular elements which engage one inside and one outside the proximal end of the coiled stem and means are provided for securing the two tubular elements together.

9. An expansible cannular as claimed in claim 8, wherein the end of the stem has a collar, and the tubular element which fits over the stem has a flange, the tabs on the caudex of the stem being nipped between the collar and the flange, the means for securing the two tubular elements together comprising a nut engaging with the outer end of the collar and having a screw-threaded engagement with the tubular element which fits over the stem.

10. An expansible cannula according to claim 3, wherein an end cap is provided which is a push fit on the distal end of the stem in the closed condition, for protecting the sharp point at the distal extremity of the stem.

* * * * *